(12) United States Patent
Lelental et al.

(10) Patent No.: US 7,820,394 B2
(45) Date of Patent: Oct. 26, 2010

(54) ULTRASENSITIVE BIOANALYTICAL ASSAYS BASED ON THE USE OF HIGH-GAIN CATALYTIC CHEMICAL AMPLIFICATION

(75) Inventors: Mark Lelental, Rochester, NY (US); Henry J. Gysling, Rochester, NY (US)

(73) Assignee: CatAssays, Rochester, NY (US)

(*) Notice: Subject to any disclaimer, the term of this patent is extended or adjusted under 35 U.S.C. 154(b) by 1220 days.

(21) Appl. No.: 11/292,585

(22) Filed: Dec. 2, 2005

(65) Prior Publication Data
US 2007/0128679 A1 Jun. 7, 2007

(51) Int. Cl.
*G01N 33/53* (2006.01)
(52) U.S. Cl. .......................... 435/7.1; 436/543
(58) Field of Classification Search ............... 435/817, 435/968; 436/37, 73, 80, 84, 149, 150, 151, 436/800, 801, 806, 904, 905
See application file for complete search history.

(56) References Cited

U.S. PATENT DOCUMENTS

| | | | | |
|---|---|---|---|---|
| 4,042,392 A | * | 8/1977 | Gysling et al. | 430/374 |
| 4,786,589 A | * | 11/1988 | Rounds | 435/5 |
| 5,494,803 A | | 2/1996 | Carbonell et al. | |
| 5,654,160 A | * | 8/1997 | Johnson | 435/7.9 |
| 2006/0025593 A1 | * | 2/2006 | Xie et al. | 546/2 |

FOREIGN PATENT DOCUMENTS

| | | |
|---|---|---|
| WO | 90/02339 A | 3/1990 |
| WO | 93/10226 A | 5/1993 |
| WO | 96/41175 A | 12/1996 |
| WO | 00/33079 A | 6/2000 |
| WO | 02/34933 A | 5/2002 |
| WO | 03/019147 A | 3/2003 |

OTHER PUBLICATIONS

Gain, Signal Gain, in The Illustrated Dictionary of Electronics, 8d., pp. 307 and 628, Gibilisco, S. Ed., McGraw-Hill Companies, Inc. (2001).*
Lelental, M. & Gysling, H.J. Formazan dye physical development: A novel high gain amplification process. J. Photographic Sci. 1978;26:135-143.*
Wu et al. (J Am. Chem. Soc. 2004, vol. 126, p. 14682-14683).*
Aluoch et al. Analytical Chem 2005 vol. 340, p. 136-144.*
Dill et al., "Immunoassays based on electrochemical detection using microelectrode arrays", Biosensors and Bioelectronics, 20, 736-742 (2004).
Chu et al., "An electrochemical stripping metalloimmunoassay based on silver-enhanced gold nanoparticle label", Biosensors and Bioelectronics, 20, 1805-1812 (2005).
Zhang et al., "Detection of ~103 DNA by an Electrochemical Enzyme-Amplified Sandwich assay with Ambient O2 as the Substrate", Anal. Chem., 76, 4093-4097 (2004).
International Search Report from corresponding International Application No. PCT/US2006/061395.

* cited by examiner

*Primary Examiner*—Jacob Cheu
(74) *Attorney, Agent, or Firm*—Heslin Rothenberg Farley & Mesiti P.C.

(57) ABSTRACT

The invention relates to ultrasensitive bioanalytical assays based on the use of high-gain catalytic chemical amplification methods. The ultrasensitive bioanalytical assays of the invention utilize high gain catalytic chemical amplification methods to detect the presence and to quantify the concentrations of target analytes labeled with specific binding reagents or biomarkers comprising a catalyst or a catalyst precursor.

20 Claims, No Drawings

ULTRASENSITIVE BIOANALYTICAL ASSAYS BASED ON THE USE OF HIGH-GAIN CATALYTIC CHEMICAL AMPLIFICATION

FIELD OF THE INVENTION

The present invention relates to ultrasensitive bioanalytical assays based on the use of high-gain catalytic chemical amplification methods. The ultrasensitive bioanalytical assays of this invention utilize high gain catalytic chemical amplification methods to detect the presence and to quantify the concentrations of target analytes labeled with specific binding reagents or biomarkers comprising a catalyst or a catalyst precursor.

BACKGROUND OF THE INVENTION

In the field of biological assays, methods are increasingly sought which allow the limits of detection and analysis of biological entities in biotic fluids to be decreased to lower concentrations, to obtain very high detection sensitivity. Thus, technological improvements have comprised not only the instrumental environment, for example the limits for detecting a signal, but also the design of the sensor reagent itself. Improvements at the signal level have reached a threshold beyond which it is no longer possible to detect the biomolecules, such threshold being of the order of nanomolar (nM) or picomolar (pM).

Nonetheless, other improvements have enabled the signal, undetectable by former technologies, to be measured owing to an amplification of the signal on which the detection principle relies. Such amplification finds its preferred application in the field of biological sensors given that the conditions implemented in biological analysis are compatible with bio-amplification systems.

Currently, two bio-amplification modes are employed in systems intended to detect, for example, immunological reactions. According to a first amplification mode, in ELISA (Enzyme Linked Immunosorbent Assays) tests, the molecule to be detected, for example an antibody that interacts with a chemical entity such as an immobilized antigen is chemically linked to an enzyme. The enzyme is used to catalyze the transformation of the detectable molecules. In the currently used ELISA systems, the enzymes which catalyze the production of chemical entities are almost always hydrolases. The water soluble reaction products are preferably detected in the whole reaction medium by measuring a characteristic property such as absorption, luminescence or bioluminescence.

In biosensors, a second amplification mode is obtained by increasing the number or mass of species detected. This amplification principle is achieved for example by linking mass markers to the molecule to be detected.

If the detection principle relies on fluorescence or absorption, fluorescent or absorbent molecules are chemically linked to the target chemical entity. By way of an example of this type of amplification, U.S. Pat. No. 5,175,270 may be cited, which discloses an amplification mechanism involving a dendrimer architecture at the surface of the sensor. The modified molecule link on each target molecule, or the marked secondary reagent link (for example colloids, nanoparticles or fluorophore-labelled secondary antibodies) will produce linear signal amplification. Latex microspheres, semiconductor nanocrystalline compounds or colloidal gold are mass markers currently used in biosensor systems. In commercial amplification systems, secondary antibodies strongly marked by fluorescent molecules contribute to increasing the signal in a linear manner.

Generally, the systems amplify the sensor signals via reactions catalyzed by an enzyme which increases the number of secondary chemical entities in the medium by catalysis (catalytic amplification for global detection). Otherwise, the sensor signals are increased either by adding mass, for mass sensitive detection, or by increasing the number of labeled molecules, which are linked to the unit.

By way of example of linear amplification at the surface of a sensor, fluorescent signal amplification may be cited. In this system the secondary antibodies are conjugated to allow detection of targets in small quantities. These two amplification modes which have been briefly described above have allowed detection sensitivity to be substantially increased, either in solution or on a surface. They do not, however, allow a sufficiently high signal to be obtained to make them useful in practice.

Binding-pair (also known as ligand-receptor, molecular recognition binding and the like) techniques play an important role in many applications of biomedical analyses and are gaining importance in the fields of environmental science, veterinary medicine, pharmaceutical research, food and water quality control and the like. For the detection of analytes at low concentrations (less than about 1 picomole analyte/sample volume analyzed) the use of fluorescent, luminescent, chemiluminescent, or electrochemiluminescent labels and detection methods are often used.

For the detection of low concentrations of analytes in the field of diagnostics, the methods of chemiluminescence and electrochemiluminescence are gaining widespread use. These methods of chemiluminescence and electrochemiluminescence provide a means to detect low concentrations of analytes by further amplifying the chemical signal of the luminescent molecules many-fold, the resulting "signal amplification" then allowing for detection of low concentrations of analytes.

In addition, the method of Polymerase Chain Reaction (PCR) and other related techniques, have gained wide use for amplifying the number of nucleic acid analytes in the sample. By the addition of appropriate enzymes, reagents, and temperature cycling methods, the number of nucleic acid analyte molecules is amplified such that the analyte can be detected by most known detection means. The high level of commercial activity in the development of new signal generation and detection systems, and the development of new types of test kits and instruments utilizing signal and analyte molecule amplification attests to the importance and need for detection methods with improved sensitivity.

SUMMARY OF THE INVENTION

In its broadest sense, the present invention provides a method for ultrasensitive bioanalytical assays to be used for biomedical diagnostics, therapy monitoring, pharmaceutical drug discovery, agricultural biotechnology, food safety testing and pathogen detection. Such assays utilize high gain catalytic chemical amplification methods to detect the presence, and to quantify the concentration of, analytes suitably labeled with specific binding reagents or biomarkers that contain a catalyst or a catalyst precursor useful for the initiation of the subsequent chemical amplification process. In a preferred embodiment, this invention is directed to ultrasensitive bioanalytical assays that are used routinely in the medical and biological sciences for various applications including cytology, disease diagnostics and monitoring of therapeutic drugs or drug abuse The detection methods of this invention can be used for a broad spectrum of biological materials such as, serum, toxins, nucleic acid, antigens, sugars, lipids, cells and viruses, as well as polysaccharides, lipopolysaccharides, proteins, glycoproteins, lipoproteins, nucleoproteins, peptides, oligonucleotides, specifically antibodies, immunoglobulins, albumin, hemoglobin, coagulation factors, peptide and protein hormones (insulin, gonadotropin, somatotropins), non-peptide hormones, interleukins, interferons and other cytokines, peptides comprising a tumor-specific epitope, cells (red blood cells), cell-surface molecules (CD antigens integrins, cell receptors), microorganisms (viruses, bacteria, parasites, molds, fungi) and their fragments, components or products, small organic molecules (digoxin, heroin, cocaine, morphine, mescaline, lysergic acid, tetrahydrocannabinol, cannabinol, steroids, pentamidine, biotin), genes, viral RNA or DNA, bacterial DNA, fungal DNA, mammalian DNA, cDNA, mRNA, RNA and DNA fragments, oligonucleotides, synthetic oligonucleotides modified oligonucleotides, single- and double-stranded nucleic acids, and natural and synthetic nucleic acids in biological fluids (serum, plasma, blood, saliva, urine), cells, cell lysates, tissues, pathogens, and organic chemicals or peptides, etc.

The methods of this invention provide means to detect and quantify the presence of selected specific labeled binding reagents or biomarkers comprising a catalyst or a catalyst precursor using a visualization chemical reaction, (e.g., an isomerization or redox reaction). The catalyst or catalyst precursor is capable of promoting such chemical amplification reactions leading to the formation of a reaction product, such as a dye, a metal or a material having luminescing (e.g., fluorescing or phosphorescing) properties. The formation of the product of this high-gain catalytic amplification reaction is subsequently detected and quantified visually or by using an appropriate instrumental analytical technique including calorimetric, fluorimetric, or chemilumometric methods.

It is an object of this invention to provide a method for detecting and quantifying the presence of an analyte of interest, comprising the steps of:

- selecting a labeled specific binding reagent or biomarker including a catalyst or a catalyst precursors and a moiety reactive with the target analyte of interest;
- reacting the target analyte of interest with the binding reagent or biomarker to form a derivative composition or composition mixture by allowing the moiety reactive with the analyte of interest to selectively form an adduct with the analyte of interest;
- separating the composition mixture into fractions.
- adding an affinity reagent for binding non-reacted binding reagent or biomarker to at least one of the fractions, and removing the bound non-reacted binding reagent or bound biomarker from the derivative composition.
- removing excess non-reacted binding reagent or biomarker from at least one of the fractions prior to detecting and quantifying the presence of the adduct; and
- detecting and quantifying the presence of the adduct using a high gain chemical amplification process initiated by the catalyst or by the catalyst precursor the latter being converted to an active catalyst in-situ by reaction with a reducing agent of a redox amplification element.

It is an another object of this invention to provide a derivatizing agent comprising a labeled specific binding reagent or biomarker for forming a derivative composition including the binding reagent or biomarker, comprising a catalyst or catalyst precursor and a moiety that forms an adduct with an analyte of interest, suitable for detection of the analyte of interest using a high gain chemical amplification process.

The catalyst or the catalyst precursor includes at least one of the transition metals including alloys with other transition metals, mixtures of such metals, group 14, 15, 16 periodic table main group elements and binary compounds of transition group metals and group 14, 15, 16 periodic table main group elements.

A derivatizing agent may comprise a plurality of agents each having a different catalyst or catalyst precursor such that different functional groups of the analyte are derivatized differently.

A derivatizing agent may have 1 or more binding sites for adduct formation with the target analyte.

It is a further object of this invention to provide a labeled specific binding reagent or biomarker comprising: a catalyst or a catalyst precursor; and a moiety selected to be reactive with an analyte of interest suitable for detection of the analyte of interest using a high gain chemical amplification process.

The catalyst or the catalyst precursor is capable of initiating a high gain oxidation-reduction ("redox") reaction.

The oxidation-reduction image-forming combination (i.e., visualization chemical reaction initiated by the presence of a catalyst in the labeled analyte) comprises:
  a) a reducing agent, and
  b) an oxidizing agent composition to produce an elemental metal, a metal compound, a dye, or a luminescent material on reaction with the reducing agent, the reducing agent and oxidizing agent being separate compounds or being components of one and the same compound, wherein the oxidizing agent comprises a leuco dye or a selenium, tellurium, bismuth, silver, copper, gold, or nickel compound.

The present invention provides the means for using a catalytic high gain chemical redox, amplification process to enhance the sensitivity and reduce the detection limits of bioanalytical assays based on the use of selective binding reagents or biomarkers capable of reacting with appropriate catalysts or catalyst precursors.

In the preferred embodiments, the catalytic transformation promotes an oxidation-reduction reaction in the visualization redox chemistry. This is preferably accomplished in a single step wherein a catalyst associated with a selective binding reagent or biomarker initiates the oxidation-reduction reaction. Alternatively, a "catalyst precursor" attached to the selective binding reagent or biomarker can be transformed initially and in-situ during the amplification process into the catalyst that then initiates the desired oxidation-reduction reaction resulting in the final visualization.

A labeled specific binding reagent or biomarker comprises a catalyst or a catalyst precursor; and a moiety selected to be reactive with an analyte of interest suitable for detection of the analyte of interest using a high gain chemical amplification process. The above catalyst or the catalyst precursor includes at least one of the transition metals including alloys with other transition metals, mixtures of such metals, group 14, 15, 16 periodic table main group elements and binary compounds of transition group metals and group 14, 15, 16 periodic table main group elements.

The binding reagent or the biomarker has one or more binding sites for adduct formation with the target analyte.

In still other embodiments, a uniformly dispersed catalyst or catalyst precursor can induce other chemical or physical changes of the visualization chemistry to provide the desired readable signal. For example, the catalyst or the catalyst precursor can react with the image precursor chemistry to cause a change in pH or in hydrophilicity or to bring about isomerization reactions. Those changes in turn can provide a readable signal. In another embodiment the high gain catalytic amplification reaction produces a product which is luminescent (e.g. fluorescent or phosphorescent), providing additional system amplification.

Other modes of using these features of the catalytic visualization chemistry of this invention would be readily apparent to one skilled in the art in view of the teaching and references noted below.

All of these various embodiments demonstrate the advantages of the present invention wherein visualization can be achieved by high-gain, chemical amplification using a wide range of catalyst or catalyst precursor-redox chemistry combinations. The incorporation of such a catalytic visualization process allows ultrasensitive bioanalytical assays with improved sensitivity compared to conventional non-catalytic methods used in the art.

DESCRIPTION OF PREFERRED EMBODIMENTS

The present invention provides means for using a catalytic high gain chemical visualization redox reactions to enhance the sensitivity of bioanalytical qualitative and quantitative methods.

The present invention provides a means for ultrasensitive bioanalytical assays based on the use of high-gain catalytic chemical amplification methods. The ultrasensitive bioanalytical assays of this invention utilize high gain catalytic amplification methods to detect the presence and to quantify the concentrations of labeled specific binding reagents or biomarkers comprising a catalyst or a catalyst precursor. The ultrasensitive bioassay chemistry of this invention comprises a specific binding reagent or biomarker, a catalyst or a catalyst precursor and high-gain catalytic chemical amplification visualization redox chemistry.

In all embodiments, the visualization redox chemistry components needed for providing a high gain chemical amplification are uniformly dispersed or dissolved in a solvent or in a mixture of solvents or in a suitable matrix, including a polymeric matrix, or an inert matrix of oxide particles.

The meaning of some of the terms used in this invention will now be described briefly.

The terms "specific binding reagent" or "biomarker" or "affinity reagent" denote chemical reagents which have specific binding interactions with various target molecules such as, for example, biomolecules.

The term "catalyst" denotes a compound or a combination of compounds that interacts with the visualization redox chemistry to reduce the activation energy for initiation of the visualization chemical reactions. The term "catalyst precursor" denotes the chemical reagent or combination of reagents, which is converted to the active catalyst in-situ by chemical reactions or by physical transformations.

The terms "labeled catalytic binding reagent" or "labeled catalytic biomarker" denote binding reagents or biomarkers comprising a catalyst or a catalyst precursor.

The term "derivative" denotes a modified chemical or biological substance formed by chemical processes that preserve the nucleus or skeleton of the parent substance.

The terms "derivatized" or "derivatizing" denote final, and ongoing states, respectively, in a chemical process of forming a modified chemical or biological substance in which the nucleus or skeleton of the parent substance is preserved.

The term "derivatizing agents" denotes the chemical reagents which are used in a chemical process of forming a modified chemical or biological substance in which the nucleus or skeleton of the parent substance is preserved.

The term "affinity" denotes a propensity to associate with via a chemical reaction or via a physical interaction such as adsorption, etc.

The term "affinity reagent" denotes the reagent that exhibits propensity to provide the association via a chemical reaction or via a physical interaction.

The term "moiety" denotes a molecule or ion, or a specific part thereof.

The term "adduct" denotes the product of the addition of a Lewis acid to a Lewis base.

The term "redox" denotes a composition or reaction comprising an oxidizing agent and a reducing agent.

The terms of "visualization redox reaction" denote a reduction-oxidation reaction in which the reaction product can be directly observed or measured based on its optical density, or can be measured based on radiation emission produced by the redox product on appropriate activation or excitation, such as by measurement of luminescence, phosphorescence, etc.

High-Gain Catalytic Chemical Amplification Chemistry

The chemistry of this invention which provides a readable signal related to the presence and concentration of the target analyte comprises two essential components: catalytic redox chemistry (i.e., a reaction pair comprising an oxidizing agent and a reducing agent) and a catalyst or a catalyst precursor. Each of these components can also have more than one component, as will be evident from the following discussion.

The "catalytic redox" chemistry includes one or more components that can be transformed or reacted in some manner in response to the ability of the catalyst to provide a readable signal. There are a number of types of precursor chemistries that can be used in the practice of this invention, and a number of such chemistries are described in more detail below. The catalyst (or catalyst precursor) is a compound or combination of compounds that transforms or interacts with the image precursor chemistry to reduce the activation energy for the reaction that produces the product which comprises a readable signal.

There are a variety of possible visualization high-gain catalytic amplification chemistries that can be used in the practice of this invention. While a number of such chemistries are described below in relation to certain embodiments of the methods of this invention, it is understood that a skilled worker in the art would readily identify other useful amplification chemistries that would produce readable chemical signals within the spirit and scope of the present invention.

Oxidation-Reduction Amplification Chemistry

The preferred amplification chemistries which produce readable chemical signals useful in the practice of this invention are based on oxidation-reduction systems. Several such chemistries are described below in more detail.

Co (III) Systems:

There are a number of known Co(III) imaging systems which can be utilized in the practice of this invention.

In one type of a redox amplification system, Co (III) coordination complexes described below can be reduced in the presence of a reducing agent (such as those described below for the tellurium imaging systems). Cobalt (2+) compounds, generated by chemical reduction of such Co(III) compounds, are useful catalysts for the initiation of such amplification systems as described in T. DoMinh, Research on Chemical Intermediates, 12, 251-262 (1989) and M. Lelental et al, J. Photogr. Sci., 36(5), 158-66 and 167-76, 1988. In a second Co(III) imaging system, a Co(III) ligand compound is chemically reduced to a labile Co(II) complex, which can then readily undergo ligand substitution with another ligand present in the matrix to form a more stable Co(III) Lewis base compound with the liberation of the initial ligands bound to the Co(III) starting complex. For example, $[Co(NH_3)_6]^{3+}$, $[Co(ethylenediamine)_3]^{3+}$ and related Co(III) complexes can be used as image precursor chemistry to undergo catalytic ligand exchange and eventually provide stable and readable Co(III) coordination compounds. Ammonia or other amines are also released during this reaction and can be used to provide useful chemical signals, for example to form a dye from a pH-sensitive dye precursor or to activate a pH-sensitive reducing agent that can then be used in a variety of redox amplification systems. Co(2+) is a catalyst for such ligand exchange reactions of Co(3+)-ligand compounds useful in such amplification chemistries. Further details of such amplification chemistry can be obtained for example in U.S. Pat. No. 4,727,008 (Lelental et al), WO 90/07730 (DoMinh), U.S. Pat. No. 4,433,037 (DoMinh), U.S. Pat. No. 4,308,341 (DoMinh), U.S. Pat. No. 4,318,977 (DoMinh), U.S. Pat. No. 4,294,912 (Adin et al). U.S. Pat. No. 4,292,399 (Adin), U.S. Pat. No. 4,273,860 (Adin and DoMinh), and Research on Chemical Intermediates, 12, 251-262 (1989) (DoMinh) all are incorporated herein by reference.

Silver-Based Redox Amplification Systems:

Useful catalytic high-gain amplification chemistry can also be composed of an oxidant comprising a non-photosensitive silver (I) compound in combination with a reducing agent, and a metal nuclei catalyst (or catalyst precursor) as described below. Such silver (I) compounds are well known in the art for use in thermographic and photothermographic imaging materials as non-photosensitive reducible silver sources. They include, but are not limited to, silver salts of thiones, triazoles, tetrazoles, imidazoles, and organic acids (fatty carboxylic acid containing 10 to 30 carbon atoms), silver salts of compounds containing mercapto or thione groups and derivatives (such as salts of mercaptotriazoles, mercaptobenzimidazoles and thioglycolic acids), silver salts of compounds containing an imino group (such as salts of benzotriazoles and imidazoles), silver salts of acetylenes, and mixtures of any of these silver salts. There are numerous publications describing such silver complexes, including U.S. Pat. No. 5,939,249 (Zou) and references cited therein, all incorporated herein by reference. Compounds which are useful silver salt oxidizing agents include, but are not limited to, silver behenate, silver stearate, silver oleate, silver laurate, silver hydroxystearate, silver caprate, silver myristate and silver palmitate.

The silver compounds act as oxidizing agents and therefore must be used in combination with one or more reducing agents that can reduce silver (I) ion in such compounds to metallic silver. A wide range of reducing agents are known for this purpose including, but not limited to, phenidone, hydroquinones, catechol, hindered bisphenols, amidoximes, hydrazides, ascorbic acid (and derivatives) and other classes of materials described, for example, in U.S. Pat. No. 5,939, 249 (noted above).

The catalysts (or catalyst precursors) used with the noted silver compounds and reducing agents are transition metals or transition metal binary nuclei as described below.

Non-Silver High Gain Redox Amplification Systems:

Similar to the silver compounds described above, a number of other metal compounds can act as oxidizing agents in thermal chemical amplification elements. Such compounds include salts or complexes of copper (II), copper (I), nickel (II), manganese (II) or (III), iron (II) or (III) and any other metal ion that can be reduced in the presence of the noted reducing agents. The metals are generally complexed with Lewis bases comprising pyrophosphates, alkanolamines, carboxylic acids, organic amines, alkoxides, aryloxides, sulfur ligands such as thiolates, xanthates, dithiocarbamates, dithiophosphates or dithiophosphinates, and organophosphines such as triphenylphosphine and tri (p-tolyl)phosphine, and other ligands well know in the art. Illustrative of such thermally developed non-silver elements are the copper physical developers described in Research Disclosure, 162, 19-20 (1977).

Reducing agents useful in these high gain redox amplification systems include amine boranes such as dimethylamine borane, diethylamine borane, triethylamine borane, phosphine boranes such as $PAr_3BH_3$ (Ar=aryl such as phenyl, p-tolyl, etc.) and pyridine borane, borohydrides such as $C[BH_4]$ (wherein C is a cation such as sodium, potassium, a tetraalkylammonium cation such as tetraethylammonium or tetraphenylphosphonium), $NaBH_3CN$, $Na_2B_{10}H_{10}$, hydrazine and substituted hydrazine derivatives, sodium hypophosphite, sodium sulfite and organic reducing agents that are well known in the photographic art.

Examples of other heavy metal salt oxidizing agents are gold stearate, mercury behenate and gold behenate.

Catalysts useful in this imaging system include the metal nuclei described below as well as binary compounds such as sulfides, borides and phosphides (such as $Cu_3P$, $CuP_2$, NiP, NiB, CoB, NiS, CuS, PdS and PtS—as described, for example, in Research Disclosure 11663, December, 1973).

More details about such redox components are provided, for example, in U.S. Pat. No. 3,935,013 (Lelental), M. Lelental, J. Electrochem. Soc., 122(4), 1975, pp. 486-490, M. Lelental, J. Catal., 32(3), 1974, pages 429-433, and M. Lelental, J. Electrochem. Soc., 120(12), 1973, pages 1650-1654, U.S. Pat. No. 3,607,351 (Lee), U.S. Pat. No. 3,650,803 (Lin), U.S. Pat. No. 3,658,661 (Minklei), Bartholomew et al, Applied Catalysis, 4, 19-29 (1982) and Uken et al, J. Catal., 65 402-415 (1980), all incorporated herein by reference.

Single Component ("Molecular") Redox Amplification

Still another type of chemical amplification element useful in this invention comprise certain metal complexes which incorporate both the metal ion oxidant and the reducing agent (as a ligand) in a single molecular metal compound or complex. Such metal complexes may include more than one type of complexing ligand including ligands that stabilize the molecule before the catalytic redox amplification reaction. Examples of such useful molecular amplification elements include, but are not limited to, metalloboranes such as $Cu(PPh_3)_2BH_4$, $Cu\{P(OPh)_3)_2\}B_3H_8$, $Cu(PPh_3)_2B_9H_{13}X)$ (wherein X is H, NCS, NCSe, $NCBPh_3$, $NCBH_3$, or $NCBH_2NCBH_3$), $Ag(PPh_3)_2BH_4$ and $Mn(CO)_5B_3H_8$ as well as those known in the art such as described in Greenwood et al, Chem. Soc Rev., 3, 231-271 (1974), Greenwood, Pure Appl. Chem, 55, 1415-30 (1983), U.S. Pat. No. 3,450,733 (Klanberg), and Meina et al, J. Chem. Soc. (Dalton Trans.), 1903-1907 (1985), Other useful molecular physical developers are metal xanthates such as $Te(S_2COR)_2$ wherein R can be a substituted or unsubstituted alkyl or aryl group and those described in the art such as Rao, Xanthates and Related Compounds, Dekker, N.Y., 1971 and Pandey et al, Thermochimica Acta, 96, 155-167 (1985). Still other useful molecular redox amplification compositions are metal complexes having the formula $ML_n$, wherein L is a 1,1-dithio ligand, M is a suitable metal ion (such as Te, Se, Cu, Cr, Mn, Co, Fe, Ni, Ag or Bi), and n is an integer of 1 to 4. Examples of such useful metal complexes with 1,1-dithio ligands include, but are not limited to, dithiophosphinates such as $M(S_2PR_2)_2$ wherein M is preferably selenium, tellurium, copper or nickel, dithiophosphates such as $M(S_2P(OR)_2)_2$ wherein M is preferably copper, nickel, selenium or tellurium, and dithiocarbamates such as $M(S_2CNR_2)_2$ wherein M is preferably copper, nickel, selenium or tellurium and those well known in the art such as described in Thorn et al, The Dithiocarbamates and Related Compounds, Elsevier, Amsterdam, 1962.

Particularly useful molecular redox amplification elements include metalloboranes, metal xanthates, metal dithiophosphinates, and metal dithiocarbamates.

These molecular redox compositions are used in combination with a metal nuclei catalyst (or a catalyst precursor), as described below, to provide a readable chemical signal resulting from the catalytic redox reaction. Such reactions may occur at room temperature, or at temperatures up to 200° C. depending on the specific chemical composition comprising the molecular amplification element. More details of molecular redox compositions are provided, for example, in H. Gysling et al, J. Photogr. Sci., 30, 55, 1982 and U.S. Pat. No. 4,188,218 (Gysling) that describes metal xanthates such as tellurium xanthates, and U.S. Pat. No. 3,505,093 (Schultz) that describes metalloboranes, these disclosures incorporated herein by reference.

Dye-Forming High Gain Redox Amplification Systems

A dye precursor (such as a leuco dye) that is reducible or oxidizable can be used as part of the amplification chemistry in combination with a reducing agent or oxidizing agent, depending upon the nature of the dye precursor. The product of such catalytic chemical amplification reactions is a dye which can be read visually or instrumentally (e.g., measurement of optical density or of fluorescence, for example).

Reducible Dye Precursors or Leuco Dyes

Examples of such compounds which are reducible include tetrazolium salts and leucophthalocyanines that can be incorporated into the analytical detection formulations and methods of this invention in combination with a suitable reducing agent and catalyst (or catalyst precursor). Upon catalytic redox reaction a chemical signal is produced by the dye product of the reaction (e.g., a formazan or phthalocyanine dye, respectively).

Useful reducing agents for this system include hydrazine (and its derivatives), amine boranes, phosphite boranes, arsine boranes, phosphine boranes, stibine boranes, boronium salts, hydroborate ions such as $BH_4^-$, $B_3H_8^-$, etc., hypophosphite, and cyanoborohydride ion.

Useful catalysts (or catalyst precursors) include the metal nuclei described below and the binary compounds noted above.

Additional details of this image chemistry can be found in U.S. Pat. No. 4,046,569 (Gysling et al), U.S. Pat. No. 4,042,392 (Gysling et al), M. Lelental et al, J. Photogr. Sci., 26(4), 1978, pp. 135-43 and M. Lelental et al, J. Photogr. Sci. 32(1), 1984, pp. 1-7, all incorporated herein by reference.

Oxidizable Leuco Dye Systems

In another embodiment of this invention, redox amplification chemistry containing an oxidizable leuco dye in combination with an oxidizing agent, such as a peroxide can be useful. Useful oxidizable leuco dyes include those of the triaryl methine class, including, for example Leucomalachite Green, Leuco Crystal Violet, and Leucoberberlin Blue.

Peroxides useful in this imaging system include hydrogen peroxide and organic peroxides such as those described in Brown, J. Org. Chem., 41, 3756, 1976, Bailey, J. Amer. Chem. Soc., 78, 3811, 1956 and Erickson, Organic Syntheses, Collect. Vol. V, Wiley, N.Y., 489 and 493 (1973). Other oxidizable leuco dyes and oxidizing agents known to those skilled in the art can also be used in this embodiment.

Catalysts (or catalyst precursors) useful in this imaging system include the metal nuclei and metal binary nuclei (for example metal sulfides, selenides, tellurides, phosphides and borides) described below as well as various metal ions such as Mn(II), Co(II) and Fe(II). Mn(II), for example, is a useful catalyst for peroxide oxidation as described in U.S. Pat. No. 4,057,427 (Enriquez et al), Research Disclosure, 15, 960, July 1977, page 58 and CA 907, 388 (Agfa). These metal ion catalysts such as Mn(II) or other useful metal ions function as homogeneous catalysts for such oxidation reactions.

Peroxide High Gain Redox Amplification Chemistry

Another catalytic amplification chemistry can include what is known in the photographic art as a color developing agent (e.g., a chemical reducing agent), and a peroxide (either hydrogen peroxide or an organic peroxide—chemical oxidizing agents). Color developing agents are compounds that, in oxidized form, will react with what are known in the photographic art as dye forming color couplers. Such color developing agents include, but are not limited to, aminophenols, p-phenylenediamines (especially N,N-dialkyl-p-phenylenediamines) and others which are well known in the art, such as EP 0 434 097A1 (published Jun. 26, 1991) and EP 0 530 921 A1 (published Mar. 10, 1993). It may be useful for the color developing agents to have one or more water-solubilizing groups as are known in the art.

Preferred color developing agents include, but are not limited to, N,N-diethyl p-phenylenediamine sulfate (KODAK Color Developing Agent CD-2), 4-amino-3-methyl-N-(2-methane sulfonamidoethyl)aniline sulfate, 4-(N-ethyl-N-β-hydroxyethylamino)-2-methylaniline sulfate (KODAK Color Developing Agent CD-4), p-hydroxyethylethylaminoaniline sulfate, 4-(N-ethyl-N-2-methanesulfonylaminoethyl)-2-methylphenylenediamine sesquisulfate (KODAK Color Developing Agent CD-3), 4-(N-ethyl-N-2-methanesulfonylaminoethyl)-2-methylphenylenediamine sesquisulfate, and others readily apparent to one skilled in the art.

Peroxides useful in this imaging system include hydrogen peroxide and organic peroxides such as those described in Brown, J. Org. Chem., 41, 3756, 1976, Bailey, J. Amer. Chem. Soc., 78, 3811, 1956 and Erickson, Organic Syntheses, Collect. Vol. V, Wiley, N.Y., pages 489 and 493 (1973).

Catalysts (or catalyst precursors) useful in these chemical elements include heterogeneous catalysts such as metals and metal binary compounds (for example sulfides, selenides, tellurides, phosphides and borides), as well as homogeneous catalysts comprising various metal ions such as Mn(II), Co(II) and Fe(II).

Tellurium High Gain Redox Amplification System

Another useful catalytic amplification chemistry of the present invention includes a tellurium(II) or tellurium(IV) compound in combination with a suitable reducing agent and metal nuclei catalyst or catalyst precursor. A range of tellurium (IV) compounds is useful as oxidizing agents. Especially useful tellurium (IV) compounds are organotellurium (IV) compounds of the general formula:

$$R_n TeX_{4-n} \qquad (I)$$

wherein R is independently, in each occurrence, a substituted or unsubstituted alkyl, substituted or unsubstituted aryl or substituted or unsubstituted acyl group, X is a halide, pseudohalide or carboxylate, and n is 1 to 4.

The halides (X) include Cl, Br and I. Pseudohalides include ligands functionally similar to halides, such as OCN, SCN, SeCN, TeCN or $N_3$. Typical carboxylates include $O_2CCH_3$ (acetate), $O_2CCF_3$ (trifluoroacetate) and $O_2CPh$ (benzoate).

Ph in all occurrences in this application designates substituted or unsubstituted phenyl. R includes, but is not limited to, substituted and unsubstituted alkyl groups (preferably those containing from 1 to 10 carbon atoms), substituted and unsubstituted aryl groups (preferably containing from 6 to 10 carbon atoms, such as phenyl and naphthyl), and substituted and unsubstituted acyl groups, preferably containing from 1 to 11 carbon atoms, such as formyl, acetyl, propanoyl, butanoyl, benzoyl, α- or β-naphthoyl, acetylacetonato, or the like).

In one particularly preferred form the formula I compound is $$TeX_2R_2 \quad (II)$$

wherein X is Cl or Br, R is and alkyl or aryl group as defined above or $CH_2C(O)Ar$, or $(R)_2$ (both occurrences of R taken together) is $-CH_2C(O)CR^1R^2C(O)CH_2-$. Ar is preferably phenyl, p-anisyl or o-anisyl. $R^1$ and $R^2$ are preferably hydrogen or methyl.

Useful compounds of this type include $Te(p\text{-}CH_3O\text{---}C_6H_4)_3Cl$ $Te(C_6H_4\text{-}p\text{-}OCH_3)_2Cl_2$ $TeCl_2[CH_2C(O)\text{-}o\text{-}CH_3O\text{---}C_6H_4]_2$ $TeCl_2[CH_2C(O)\text{-}p\text{-}CH_3O\text{---}C_6H_4]_2$ $TeCl_2[CH_2C(O)\text{---}C_6H_5]_2$ $TeBr_2[CH_2C_6H_5]_2$ $TeCl_2[CH_2C(O)C(CH_3)_2C(O)CH_2]$ and $TeCl_2[CH_2C(O)CH_2C(O)CH_2]$.

The described complexes of tellurium (IV) generally have a coordination number of four although compounds containing an organic group R that is functionalized with one or more Lewis base substituents may have coordination numbers greater than 4 [for example the organotellurium-(IV) chelate, $TeCl_3$-(2,6-diacetylpyridine-C,N,O] that has a coordination number of 6, as taught in U.S. Pat. No. 4,239,846 (Gysling et al) and in H. Gysling et al, J. Organomet. Chem., 184, 417(1980)].

The term organotellurium (IV) compound as used herein is intended to include any type of bonding or complexing mechanism which enables the resulting material to provide oxidizing agent properties and the described oxidation-reduction amplification element combination when combined with a reducing agent, such as an organic reducing agent. These redox elements can be introduced as a solution or incorporated in a polymeric matrix coated on a suitable substrate. In some cases the exact bonding of the described tellurium (IV) compound is not fully understood. Accordingly, the term "compound" is intended to include salts and other forms of bonding in the desired oxidation-reduction image precursor combination. The term organotellurium compound also is intended to include neutral complexes or salts of non-neutral complexes.

Useful organotellurium (IV) compounds are described, for instance, in K. Irgolic, The Organic Chemistry of Tellurium, Gordon and Breach Science Publishers, N.Y., N.Y., 1974 and K. Irgolic, J. Organometal. Chem., 103, 91(1975), 130, 411 (1977), 158, 267(1978), 189, 65(1980), 203, 367(1980), The Chemistry of Organic Selenium and Tellurium Compounds, Vol. 1 (1986) and Vol. 2 (1987), Patai and Rappoport (Eds.), Wiley, N.Y., and Irgolic, Organotellurium Compounds in Methods of Organic Chemistry (Houben-Weyl), Vol. E12b, D. Klamann (Ed), Georg Thieme, Verlag, N.Y., 1990.

The selection of an optimum organotellurium (IV) compound for an amplification element of this invention will depend upon such factors as the particular reducing agent in the amplification element, processing conditions, and the like.

Especially useful organotellurium (IV) oxidizing agents include $TeX_2(CH_2C_6H_5)_2$ (wherein X is Cl, Br, I or acetyloxy), $TeCl_2[CH_2C(O)Ar]_2$ (wherein Ar is phenyl, p-anisyl or o-anisyl), and $TeX_2 [CH_2C(O)CR^1R^2C(O)CH_2]$ [wherein X is halide, pseudohalide or carboxylate as described above, and $R^1$ and $R^2$ are H, alkyl (such as methyl) or aryl].

Tellurium (II) coordination compounds containing 1,1-dithio ligands are also useful as oxidants in this invention. Such compounds include, but are not limited to, those having the following formula:

$$Te(S_2X)_2$$

wherein X is COR (xanthates, and R is an alkyl or aryl group as defined above), $CNR_2$ (dithiocarbamates, and R is an alkyl or aryl group as defined above), $RP_2$ (dithiophosphinates, and R is an alkyl or aryl group as defined above), $P(OR)_2$ (dithiophosphates, and R is an alkyl or aryl group as defined above), or CR (dithiocarboxylates, and R is an alkyl or aryl group as defined above).

These and other useful Te(II) compounds have been described for example in M. Lelental et al, J. Photogr. Sci., 28 109-218 (1980), H. Gysling et al, J. Photogr. Sci., 30, 55-65 (1982), Haiduc et al, Chem. Rev., 94, 301-326 (1994), U.S. Pat. No. 4,251,623 (Gysling), and U.S. Pat. No. 4,152,155 (Lelental et al).

Reducing Agents

The redox formulation of this invention can comprise a variety of reducing agents. These reducing agents can be organic reducing agents, inorganic reducing agents or combinations of both, with organic reducing agents being preferred. Reducing agents that are especially useful are typically silver halide developing agents. Examples of useful reducing agents include, but are not limited to, phenolic reducing agents (such as polyhydroxybenzenes, including, for instance, hydroquinone, alkyl-substituted hydroquinones, including tertiary butyl hydroquinone, methyl hydroquinone, 2,5-dimethylhydroquinone and 2,6-dimethylhydroquinone; catechols and pyrogallols; chloro-substituted hydroquinones, such as chlorohydroquinone or dichlorohydroquinone; alkoxy-substituted hydroquinones, such as methoxyhydroquinone or ethoxyhydroquinone; aminophenol reducing agents such as 2,4-diaminophenols and methylaminophenols), ascorbic acid reducing agents (such as ascorbic acid, ascorbic acid ketals and ascorbic acid derivatives), hydroxylamine reducing agents, 3-pyrazolidone reducing agents (such as 1-phenyl-3-pyrazolidone and 4-methyl-4-hydroxymethyl 1-phenyl-3-pyrazolidone), reductone reducing agents (such as 2-hydroxy-5-methyl-3-piperidino-2-cyclopenitenone), sulfonamidophenol reducing agents such as described those in Research Disclosure, January 1973, pages 16-21 and others readily apparent to one skilled in the art. Inorganic reducing agents can include borane type reductants such as $LBH_3$ where L=an amine or organophosphine (for example $PPh_3BH_3$, $Me_2HNBH_3$, $Me_3NBH_3$, $Et_3NBH_3$, and pyridine$BH_3$) as, for example, described in Lane, Aldrichimica Acta, 6, 51-58 (1973) and WO 97/49841 A1 (Corella et al), and hydroborate salts, including $BH_4^{1-}$ salts such as $KBH_4$, $Et_4NBH_4$ and $[(PPh_3)_2N]BH_4$ and $K[B_3H_8]$, $Cs[B_9H_{14}]$, $Na_2 [B_{10}H_{10}]$, and related hydroborate salts as described in Kane et al, J. Amer. Chem Soc., 92, 2571-2 (1970), U.S. Pat. No. 3,406,019 (Muetterties), Klanberg et al, Inorg. Chem., 7, 2272-8 (1968), and Klanberg et al, Inorg. Synth., 11, 24-33 (1968). Useful inorganic reducing agents also include, for example, those described in U.S. Pat. No. 3,598,587 (Yudelson et al). Combinations of reducing agents can be employed, if desired.

A broad range of concentrations of the reducing agents is useful in the formulations of the invention. The optimum concentration will depend upon such factors, as the particular composition, amplification reaction temperature, desired readable signal, and the like. Typically a concentration of from about 0.01 to about 10 moles of reducing agent per mole of organotellurium oxidizing agent is employed in the element, preferably a concentration of from about 0.1 to about 5 moles of reducing agent per mole of described oxidizing agent is used.

Catalysts and Catalyst Precursors

The elements of this invention must include a catalyst or a catalyst precursor of some type. For example, one or more metal-containing catalytically active particles or metal nuclei or their chemical precursors can be used. The catalyst-providing component can be any metal, especially transition metals including alloys with other transition metals, group 14, 15 or 16 periodic table main group elements, mixtures of such metals, metal binary compounds or metal salts or complexes that function as the desired redox catalyst, or provide the desired catalytically active nuclei by means of some chemical transformation of a catalyst precursor. The concentration of catalyst component can be from about 0.0001 to about 1.0 mole of metal compound per mole of oxidizing agent in the oxidation-reduction combination that gives the readable signal with the preferred range being from about 0.001 to about 0.1 mole per mole of oxidizing agent.

Palladium metal nuclei are preferred catalysts for this invention since they provide catalytic sites that promote formation of the readable chemical signal which is the product of the catalytic amplification reaction (e.g., typically a transition metal such as Cu or Ni or a main group element such as tellurium, or an organic or organometallic dye). Other nuclei for promoting this process can alternatively be employed as catalysts. Such nuclei include chromium, iron, cobalt, nickel, copper, selenium, silver, tin, tellurium, iridium, ruthenium, rhenium, platinum, rhodium, and gold. Copper, tellurium, palladium, platinum, rhodium, iridium, gold and silver are preferred. The nuclei can be in the form of small clusters of the metal, $M_n$ (n=2-100 ideally) or present as metal binary compounds, such as phosphides, sulfides, selenides, tellurides, oxides or the like. The palladium catalyst can be incorporated in the process of this invention as preformed metal nuclei or the nuclei can be provided from any convenient precursor source, such as compounds that are decomposable through various means to the desired metal nuclei. Such decomposable compounds include, but are not limited to, $K_2Pd(C_2O_4)_2$, $PdCl_2$, $K_3Co(C_2O_4)_3$, $K_2[MCl_4]$ wherein M is Pd or Pt, $[Et_4N]_2[MCl_4]$ wherein M is Pd or Pt, $M(PR_3)_2Cl_2$ wherein M is Pd or Pt, R is alkyl or aryl, $M(acac)_2(CO)_2$ wherein M is Rh or Ir, "acac" is acetylacetonate; $[Co(NH_3)_5N_3]Cl_2$, $Se(S_2CO\text{-}iso\text{-}C_3H_7)_2$, $Te[S_2P(OCH_3)_2]_2$, $K_2Pt[(C_2O_4)_2]$, $[Pd[P(C_6H_5)_3]_2(C_2O_4)]$, $\{Cu[P(OCH_3)_3]_4\}B(C_6H_5)_4$, $\{Cu[P(OCH_3)_3]_2BH_3CN\}_2$, $Cu[Sb(C_6H_5)_3]_3Cl$ and $[Cu(ethylenediamine)_2][B(C_6H_5)_4]_2$. Other useful Pd complexes are described in U.S. Pat. No. 3,719,490 (Yudelson et al), U.S. Pat. No. 4,287,354 (Gysling) and U.S. Pat. No. 4,258,138 (Gysling), and Research Disclosure, Item 13705, September 1975. Other useful Cu complexes are described in U.S. Pat. No. 3,859,092 (Gysling et al) and U.S. Pat. No. 3,860,501 (Gysling), U.S. Pat. No. 3,880,724 (Gysling), U.S. Pat. No. 3,9237,055 (Gysling), and Barnard et al, Palladium in *Comprehensive Coordination Chemistry*, Vol. 5, pp. 1099-1129, G. Wilkinson, Gillard, and McCleverty (Eds.), Pergamon Press, New York, 1987, all of the disclosures of which are incorporated herein by reference. Such catalyst precursor compositions can be converted to the active catalyst for the chemical amplification reaction by various means well know in the art, such as chemical reduction or exposure to actinic radiation such, as UV radiation or visible region light, or by heating to a suitable temperature.

Binary combinations of these metals are also efficient initiators or catalysts for the amplification chemistries of this invention because of their high degree of catalytic activity. Other metal-containing catalytically active compounds or catalyst precursors that can initiate the amplification reactions are also useful for forming readable signals according to the invention. Other metal compounds that provide catalytic nuclei that are useful include chromium, iron, cobalt, nickel, copper, selenium, palladium, silver, tin, tellurium, iridium, ruthenium, rhenium, platinum, rhodium and gold compounds and combinations of these compounds. In still another embodiment, the metal catalyst precursor, for example a Pd(II) or Pt(II) compound, is spontaneously reduced to the elemental metal by the reducing agent of the redox chemistry used as the chemical amplification element.

Specific Binding Reagent or Biomarker Labelled with Catalyst or Catalyst Precursor The chemical amplification of the target analyte is achieved by initially selectively binding a reagent or a biomarker that incorporates a catalyst or catalyst precursor as described above. The analyte of interest may contain more than one functionality, which can form stable derivative compositions with the catalytic binding reagent or the catalytic biomarker by a chemical, physical or electrostatic interaction. Binding reagents or biomarkers which have specific reactive groups that facilitate binding interactions, including covalent binding, ionic binding, or adduct formation, with various biomolecules are well known in the bioanalytical art. Such specific interaction include antigen-antibody interactions which are well known in the art, as well as molecules which can specifically bind to tumor cells such as those that are used in photodynamic chemotherapy as described in M. Detty et al. Bioorganic & Medicinal Chemistry (2004), 12(10), 2537-2544, U.S. Patent Application 2003069219 A1, Journal of Medicinal Chemistry (2002), 45(23), 5123-5135, Journal of Medicinal Chemistry (2002), 45(2), 449-461, Journal of Medicinal Chemistry (2000), 43(23), 4488-4498, and Proceedings of SPIE—The International Society for Optical Engineering (1988), 847 (New Dir. Photodyn. Ther.), 68-73.

Suitable catalysts or catalyst precursors can be attached to the specific binding agent using electrostatic interactions or Lewis acid—Lewis base interactions. Such catalysts include small clusters of transition metals, $M_n$ such as M=Pd(0), Pt(0), Au(0), Cu(0), and Ag(0), and typically n=1-100. The catalyst or catalyst precursor incorporated on the selective binding reagent (SBR) can also comprise a transition metal ion which can function as a homogenous catalyst (e.g., Mn(2+) which can catalyze peroxide oxidations of leuco dyes to give the corresponding dyes) or a transition metal ion which can be chemically reduced in-situ by the reducing agent of the redox amplification element to give the Mn catalyst described above (metal=metal or metal binary material, and n=number of atom necessary to produce a catalyst cluster particle of sufficient size to function as an active catalyst). The use of Pd-(2+) as a catalyst precursor reagent attached to the SBR is a preferred example of this embodiment since this species can be readily reduced in-situ to Pd(0) which is a very active catalyst for various catalytic reduction reactions which are useful as chemical amplification elements in this invention. Pd(2+)-protein specific interactions are well known in the art and can be used as the binding mechanism in the Pd(2+) interaction with the SBR. Such Pd(2+) interactions with SBR binding sites have been described, for example, in J. S. Yudelson and T. M. Johnson, U.S. Pat. No. 4,552,848 (1985), J. S. Yudelson, U.S. Pat. No. 4,672,043 (1987), and J. S. Yudelson, BioTechniques (1984), 23(1), 42, 44-5, 47, A. A. Saboury et al, Journal of the Chinese Chemical Society (Taipei) (1999), 46(6), 917-922. J. L. Butour et al, Chemico-Biological Interactions (1997), 104(2,3), 165-178, and E. N. Zhmareva et al, Ukrainskii BiokhimicheskiiZhurnal (1996 May-June), 68(3), 74-9, In contrast to prior art detection methods, which most commonly rely on the radiation absorption or emission of labeled analyte, the present invention is based on the chemical modification or labeling of the analyte by binding to a catalyst or catalyst precursor.

The resulting labeled analyte is then treated with a chemical amplification system, such as a redox system comprising a solution of an oxidizing agent and a reducing agent. The redox reaction associated with the redox system is initiated by the catalyst incorporated in the labeled analyte. In one embodiment of this invention the analyte is labeled with a catalyst precursor which is initially, and in-situ, converted to an active catalyst by a component of the solution redox system. High sensitivity results from the high affinity of an analyte towards a labeled binding reagent or labeled biomarker and catalytic redox amplification reaction which provides a readable signal. Such amplification reactions, typically having amplification factors of $10^7$-$10^9$ permit detection of an analyte at analyte molar concentration in a range of from $10^{-15}$ to $10^{-3}$. This range of molar concentrations permits detection of quantities of the analyte of interest in a range of from $10^{-14}$ to $10^{-2}$ grams. The chemical amplification system in a solution or in a dispersion can be operated at a temperature up to 200° C.

In another embodiment the chemical amplification system is incorporated in a polymeric matrix in the form of a layer on a suitable substrate such as a paper or polymeric film base and the analyte, labeled with the catalyst or catalyst precursor, is applied to the system containing the chemical amplification element and the chemical amplification reaction occurs spontaneously at room temperature or by heating this system comprising the analyte and the selective binding agent containing the catalyst or catalyst precursor to a temperature up to 200° C. Other means of activating a catalyst precursor to generation of the active catalyst that are well know in the art are also included in the scope of this invention (e.g., exposure of the catalyst precursor to suitable radiation such as UV radiation or visible light, etc.).

From the detailed description it will be apparent that the present invention is directed at detecting and quantifying trace amounts of an analyte of interest also referred to as a target analyte of interest. In all embodiments of the invention the detection of such trace amounts is achieved by a high gain redox chemical amplification process initiated by a catalyst. The process includes selecting a labeled specific binding reagent or biomarker which includes a catalyst and a moiety reactive with the analyte of interest. The analyte of interest is reacted with the binding reagent to form a derivative composition or composition mixture by allowing the moiety to selectively form an adduct with the analyte. Alternatively, a catalyst precursor can be used which is converted to an active catalyst in-situ by reaction with a reducing agent of a redox amplification element. The composition mixture can be separated into fractions and the presence of the adduct is detected and quantified in at least one of the fractions.

The catalyst or catalyst precursor is bound to the binding reagent or biomarker to produce a catalytic binding reagent or a catalytic biomarker prior to forming the derivative composition or composition mixture.

The catalyst or a catalyst precursor can be covalently bound to the biomarker. The biomarker moiety comprising the catalyst or catalyst precursor forms a chemical adduct with the analyte of interest.

Preferred catalysts or catalyst precursors contain at least one of the metals selected from copper, gold, silver, tellurium, bismuth, palladium, platinum, rhodium and iridium, and including alloys and mixtures of such metals, or a binary compound of one or more of the such metals with groups 14, 15 or 16 of the periodic table elements.

A particularly preferred catalyst or catalyst precursor contains palladium.

A catalytic binding reagent or a catalytic biomarker reacts specifically with a functional group of the analyte of interest at molar concentrations of the analyte in a range from $10^{-15}$ to $10^{-3}$. Thus, an analyte of interest can be detected in a derivative composition at a molar concentration as low as one part per trillion. The range of molar concentrations of the analyte permits detection of quantities of the analyte of interest in a range of $10^{-14}$ to $10^{-2}$ grams.

A catalyst precursor can be an organometallic or coordination compound.

A preferred high gain chemical amplification formulation comprises a reducible or oxidizable leuco dye, and an oxidizing or a reducing agent, respectively, that upon contact with catalyst or catalyst precursor is capable of catalytic generation of a corresponding dye.

The leuco dye and an oxidizing or a reducing agent are dissolved or dispersed in water or an organic solvent or a polymeric matrix. An organic solvent can be an alcohol, for example methanol, or an ester.

A particularly preferred high gain amplification process is based on the formation of a formazan dye or a metalized formazan dye via catalytic reduction of a corresponding tetrazolium salt by the reducing agent that does not spontaneously reduce said tetrazolium salt, said reducing agent being selected from the group consisting of hydrazines, amine boranes, phosphite boranes, arsine boranes, phosphine boranes, stibine boranes, boronium salts, hydroborate ions such as $BH_4^-$, $B_3H_8^-$, etc., hypophosphite, and cyanoborohydride ion.

Another preferred high gain amplification process is based on the formation of a phthalocyanine dye via catalytic reduction of a leucophthalocyanine dye by the reducing agent that does not spontaneously reduce said leucophthalocyanine dye, said reducing agent being selected from the group consisting of amine boranes, phosphite boranes, pyridine boranes, phosphine boranes, stibine boranes, boronium salts, borohydride ion, and cyanoborohydride ion.

The most preferred high gain amplification process is based on formation of a formazan dye from the corresponding tetrazolium salt using palladium metal catalyst or palladium organometallic or coordination compound catalyst precursor. A preferred redox combination is 2,3,5-triphenyl-2H-tetrazolium chloride leuco dye, and a hydrazine or an amine borane such as dimethylamine borane reducing agent.

Another most preferred high gain amplification process is based on formation of a nickel phthalocyanine dye using palladium metal catalyst or palladium organometallic or coordination compound catalyst precursor, nickel leucophthalocyanine and dimethylamine borane reducing agent.

Sample Preparation

In general the analytical problem usually involves the detection of "trace" amounts of analytes in a very complex matrix of potential interferences. It is, therefore, critical to choose a suitable sample preparation technique for the particular class of analyte of interest in the particular biomatrix which could be a biofluid or a tissue. The various procedures of sample collection and preparation that have been developed for specific bioassays would be applicable in the methods of this invention. The sample collection may include reagents and/or treatments for neutralization of infectious agents, stabilization of the specimen or sample, pH adjustments, and the like. Stabilization and pH adjustment treatments may include, addition of buffering agents, preservatives, biocides, and the like. For those embodiments where whole cells, viruses or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat, etc., into a crude extract, followed by additional treatments to prepare the sample for subsequent operations, e.g., denaturation of contaminating (DNA binding) proteins, purification, filtration, desalting, and the like. Liberation of nucleic acids from the sample cells or viruses, and denaturation of DNA binding proteins may generally be performed by physical or chemical methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins.

Alternatively, physical methods may be used to extract the nucleic acids and denature DNA binding proteins. U.S. Pat. No. 5,304,487, herein incorporated by reference, discusses the use of physical protrusions within microchannels or sharp edged particles within a chamber or channel to pierce cell membranes and extract their contents. More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the scope of the present invention to effect cell lysis/extraction, including, e.g., subjecting cells to ultrasonic agitation, or forcing cells through microgeometry apertures, thereby subjecting the cells to high shear stress resulting in rupture.

Following extraction, it will often be desirable to separate the nucleic acids from other elements of the crude extract, e.g., denatured proteins, cell membrane particles, and the like. Removal of particulate matter is generally accomplished by filtration, flocculation or the like. A variety of filter types may be readily incorporated into a device. Further, where chemical denaturing methods are used, it may be desirable to desalt the sample prior to proceeding to the next step. Desalting of the sample, and isolation of the nucleic acid, may generally be carried out in a single step, e.g., by binding the nucleic acids to a solid phase and washing away the contaminating salts or performing gel filtration chromatography on the sample. Suitable solid supports for nucleic acid binding include, e.g., diatomaceous earth, silica, or the like. Suitable gel exclusion media are also well known in the art and are commercially available from, e.g., Pharmacia and Sigma Chemical. This isolation and/or gel filtration/desalting may be carried out in an additional chamber, or alternatively, the particular chromatographic media may be incorporated in a channel or fluid passage leading to a subsequent reaction chamber The sample preparation process may include removal of an excess of non-reacted binding reagent or biomarker from at least one of the fractions prior to detecting and quantifying the presence of the adduct.

The separation of the derivative composition or composition mixture may be carried out using a chromatography technique selected from the group consisting of liquid chromatography (LC), thin layer chromatography (TLC), gas chromatography (GC), ion exchange chromatography (IEC), capillary electrophoresis (CE), size exclusion chromatography, high performance liquid chromatography (HPLC), gel electrophoresis, and affinity chromatography.

The separating process of the derivative mixture may be stopped prior to detecting and quantifying the presence of the adduct.

The removal of the bound non-reacted binding reagent or biomarker from the derivative composition may be achieved using methods that include filtering techniques or sedimentation techniques.

In an another embodiment of this invention the catalytic bioanalytical assay can be done in a bi- or multilayer element in which 2 or more layers are coated on a rigid or flexible support. In such a bi- or multilayer element, for example, a layer incorporating the high gain, redox, chemical amplification formulation could be coated on a suitable support, under a separate layer comprising a spreading layer to allow uniform addressing of the former detection layer by an applied solution of the test analyte comprising a catalyst or a catalyst precursor. After application of the test analyte-labeled catalytic reagent solution, a catalytic reaction selected from the types described in this invention could result in direct formation of a readable image density under ambient conditions. In other embodiments the element, after application of the solution containing the test analyte-catalytic binding reagent combination, is heated or otherwise activated by a suitable energy source to initiate the catalytic detection reaction and produce the readable signal. The product of such catalytic detection reactions can be read through the top layer or through the bottom layer, depending on the properties of the specific layers employed in such a bi- or multilayer detection element. The use of a flexible support, such as a polymeric support, has the advantage of being useful in a convenient roll coating manufacturing process. Examples of dry analytical assay elements are commercially available, such as Kodak's Ektachem Clinical Chemistry slides described in H. G. Curme et al, Clinical Chemistry, 43(9) 1647-1652 (1997), H. G. Curme et al, Clinical Chemistry, 24(8), 1335-1342 (1978) and R. W. Spayd et al, Clinical Chemistry 24(8), 1343-1350 (1978).

The Ektachem test element provides for transport and separation of heterogeneous fluid samples and quantitative analysis of biological samples by various measurements. This multilayer test element, which can be especially adapted for use in a disposable blood sampling fixture, comprises at least three functional components: (1) a wicking element for reception of the whole blood sample and transport of the sample to a dry chemistry reagent system in an adjacent layer, (2) a porous membrane which has been impregnated with a dry chemistry reagent system specific for analysis of an analyte within the whole blood applied test sample, and (3) a barrier layer is provided between the wicking layer and the porous membrane to preclude contact between these 2 layers. In the preferred embodiments, an aperture is cut or formed in the barrier layer to allow for the flow of sample from the wick to the surface of the porous membrane. Such transport of sample does not, however, involve or contemplate physical contact between the wick and the membrane in the area of the aperture. This test strip is suitable for use in a disposable fixture designed for self-collection and testing of the whole blood sample for one or more constituents (e.g., glucose).

Certain known dry multilayer immunoassay elements include a layer comprising a leuco dye. In the course of an assay for a specified analyte in a sample, the leuco dye, in the presence of hydrogen peroxide and a material having peroxidase activity, is oxidized to a colored form. As is well known the reflection density of the color is proportional to the concentration of analyte in the sample. The reflection density can be measured using a reflectometer.

Typical leuco dyes used for this purpose are highly aromatic leuco dyes that cannot be dissolved and deposited or coated as an aqueous solution. Such leuco dyes are the diaryl- and triarylmethanes of U.S. Pat. No. 4,670,385; and the diaryl- and triarylimidazole dyes of U.S. Pat. No. 4,089,747 and U.S. Pat. No. 5,024,935. Such leuco dyes have been coated as dispersions by dissolving the leuco dye in an organic solvent (methanol or dimethyl sulfoxide) and reprecipitating in an aqueous polymer solution to produce a coating composition of the oxidizable leuco dye in a polymer solution; or dissolving the leuco dye in a "coupler solvent" (diethyl lauramide) and redispersing the coupler solvent solution in an aqueous solution. U.S. Pat. Nos. 4,670,385; 4,089,747; 5,024,935; 4,089,747 and 4,258,001 describe further details and cite references to other literature describing this technology.

Although preferred embodiments of the invention are described herein in detail, it will be understood by those skilled in the art that variations may be made thereto without departing from the spirit of the invention or from the scope of the appended claims.

What is claimed is:

1. A method for detecting and quantifying the presence of a target analyte of interest by a high gain redox chemical amplification reaction having an amplification factor of $10^7$ to $10^9$, said method comprising the steps of:
   selecting a biomarker that comprises a metal catalyst or a metal catalyst precursor and a moiety that is selectively reactive with the target analyte of interest;
   reacting said target analyte of interest with said reactive moiety of said biomarker to selectively form a first reaction product comprising said metal catalyst or a metal catalyst precursor contained in a reaction mixture;
   separating the reaction mixture into two or more fractions; and
   detecting and quantifying the target analyte of interest subjecting said first reaction product present in at least one of said fractions to a high gain redox chemical amplification formulation comprising a leuco dye and a reducing agent to produce a second reaction product in the form of a dye, said dye being formed in a reaction catalyzed by said first reaction product.

2. The method of claim 1, further comprising: binding the biomarker with a catalyst or catalyst precursor to produce a metal catalyst- or metal catalyst precursor-labeled biomarker prior to forming a first reaction product in the reaction mixture.

3. The method of claim 2, wherein the metal catalyst or the metal catalyst precursor is covalently or electrostatically bound to the biomarker.

4. The method of claim 1, wherein the biomarker reacts specifically with a functional group of the target analyte of interest to give a stable reaction product, at concentrations of said analyte of $10^{-15}$ to $10^{-3}$ moles per liter, or $10^{-14}$ to $10^{-2}$ grams per liter.

5. The method of claim 1 wherein said metal catalyst or metal catalyst precursor contains at least one of the elements selected from the group consisting of copper, gold, silver, palladium, platinum, rhodium, iridium, and alloys and mixtures of said elements.

6. The method of claim 1 wherein said metal catalyst precursor is an organometallic or coordination compound containing at least one of the elements selected from copper, gold, silver, palladium, platinum, rhodium, iridium, and mixtures of said compounds.

7. The method of claim 1 wherein said high gain redox chemical amplification formulation is dissolved or dispersed in a liquid and comprises a reducible leuco dye and a reducing agent that, upon contact with said first reaction product, produces said second reaction product in the form of a dye.

8. The method of claim 7 wherein said high gain redox chemical amplification formulation produces the second reaction product that is a formazan dye or a metalized formazan dye via metal catalyzed reduction of a corresponding tetrazolium salt by a reducing agent that does not spontaneously reduce said tetrazolium salt, said reducing agent being selected from the group consisting of amine boranes, pyridine boranes, and boronium salts.

9. The method of claim 1, wherein said moiety that is selectively reactive with said target analyte comprises an antibody having an affinity for an antigen of interest in said analyte.

10. The method of claim 2, wherein the target analyte of interest contains at least one functionality that can form stable first reaction products with said metal catalyst- or metal catalyst precursor-labeled biomarker by a chemical, physical or electrostatic interaction.

11. The method of claim 2, further comprising: removing excess non-reacted metal catalyst- or metal catalyst precursor-labeled biomarker from said reaction mixture prior to detecting and quantifying said first reaction product.

12. The method of claim 11, further comprising: adding an affinity reagent for binding the non-reacted metal catalyst- or metal catalyst precursor-labeled biomarker, thereby removing said non-reacted metal catalyst- or metal catalyst precursor-labeled biomarker from said reaction mixture.

13. A method for detecting a labeled analyte of interest in a mixture, said method comprising the steps of:
   obtaining a biomarker that comprises a metal catalyst or a metal catalyst precursor and a moiety that is selectively reactive with a target analyte;
   producing a mixture containing the labeled analyte of interest that results from reaction of said moiety and said target analyte;
   obtaining fractions of said mixture, identifying a fraction of said mixture that contains said metal catalyst or the metal catalyst precursor labeled analyte of interest using a high gain redox chemical amplification reaction having an amplification factor of $10^7$ to $10^9$, said high gain redox chemical amplification reaction resulting from adding a high gain redox chemical amplification formulation comprising a leuco dye and a reducing agent to reduce a portion of the leuco dye to a water-soluble dye, said portion being related to the concentration of the labeled analyte of interest;

quantifying optically a signal of the water soluble dye; and determining from the signal the concentration of the labeled analyte of interest.

14. The method of claim 6 wherein said element is palladium.

15. The method of claim 5 wherein said element is palladium.

16. A method for detecting and quantifying a target analyte of interest in a mixture by a high gain redox chemical amplification formulation, said method comprising the steps of:

selecting a biomarker that comprises a metal catalyst or a metal catalyst precursor and a moiety that is selectively reactive with the target analyte of interest;

reacting said target analyte of interest with said reactive moiety of said biomarker to selectively form a first reaction product contained in a reaction mixture;

separating the reaction mixture into two or more fractions; and detecting and quantifying the first reaction product present in at least one of the fractions by said high gain redox chemical amplification reaction, said amplification reaction having an amplification factor of $10^7$ to $10^9$ and initiated by said metal catalyst or metal catalyst precursor, said catalyst precursor being converted to an active catalyst in-situ by reaction with a reducing agent of said high gain redox chemical amplification formulation;

wherein said target analyte of interest is present in said mixture in a concentration of $10^{-15}$ to $10^{-3}$ moles per liter, or $10^{-14}$ to $10^{-2}$ grams per liter; and wherein said detecting and quantifying said first reaction product comprise adding a high gain redox chemical amplification formulation comprising a leuco dye and a reducing agent to thereby produce a second reaction product in the form of a dye, said dye being produced in a reaction catalyzed by said first reactions product;

quantifying optically a signal of said dye from the second reaction product; and determining from the signal a concentration of the target analyte of interest.

17. The method of claim 1 wherein said high gain redox chemical amplification reaction is carried out in a solution or dispersion containing a reducible leuco dye and a reducing agent at a temperature of about 200° C.

18. The method of claim 1 wherein said high gain redox chemical amplification reaction is carried out in a polymeric layer containing a reducible leuco dye and a reducing agent at a temperature of about 200° C.

19. The method of claim 8 wherein said high gain redox chemical amplification reaction produces a water soluble formazan dye.

20. The method of claim 8 wherein said high gain redox chemical amplification reaction produces a water soluble, luminescent formazan dye.

* * * * *